(12) United States Patent
Katsuhiro (10) Patent No.: US 10,891,720 B2
(45) Date of Patent: Jan. 12, 2021

(54) CROSS DIRECTIONAL BILATERAL FILTER FOR CT RADIATION DOSE REDUCTION

(71) Applicant: AlgoMedica, Inc., Sunnyvale, CA (US)

(72) Inventor: Ichikawa Katsuhiro, Ishikawa (JP)

(73) Assignee: AlgoMedica, Inc., Sunnyvale, CA (US)

( * ) Notice: Subject to any disclaimer, the term of this patent is extended or adjusted under 35 U.S.C. 154(b) by 79 days.

(21) Appl. No.: 16/374,490

(22) Filed: Apr. 3, 2019

(65) Prior Publication Data
US 2019/0311465 A1    Oct. 10, 2019

Related U.S. Application Data

(60) Provisional application No. 62/652,787, filed on Apr. 4, 2018, provisional application No. 62/654,158, filed on Apr. 6, 2018.

(51) Int. Cl.
*G06T 5/00* (2006.01)
*G06T 11/00* (2006.01)
*A61B 6/00* (2006.01)
*A61B 6/03* (2006.01)

(52) U.S. Cl.
CPC ............ *G06T 5/002* (2013.01); *A61B 6/5258* (2013.01); *A61B 6/542* (2013.01); *G06T 11/005* (2013.01); *A61B 6/032* (2013.01); *A61B 6/461* (2013.01); *G06T 5/003* (2013.01); *G06T 2207/10072* (2013.01); *G06T 2207/10081* (2013.01); *G06T 2207/10116* (2013.01); *G06T 2207/20004* (2013.01); *G06T 2207/20028* (2013.01); *G06T 2211/40* (2013.01)

(58) Field of Classification Search
CPC ....... G06T 5/002; G06T 5/003; G06T 11/005; G06T 2207/10081; G06T 2207/20004; G06T 2211/40; A61B 6/5258; A61B 6/542; A61B 6/032; A61B 6/461
See application file for complete search history.

(56) References Cited

U.S. PATENT DOCUMENTS

| 5,835,562 A | 11/1998 | Ramsdell et al. |
|---|---|---|
| 7,245,755 B1 | 7/2007 | Pan et al. |
| 2010/0272340 A1 | 10/2010 | Bar-Aviv et al. |
| 2011/0110601 A1* | 5/2011 | Hong .................. G06T 5/20 382/255 |
| 2011/0286651 A1 | 11/2011 | Yu et al. |
| 2012/0224760 A1 | 9/2012 | Goshen et al. |

(Continued)

FOREIGN PATENT DOCUMENTS

WO    2017080847 A1    5/2017

OTHER PUBLICATIONS

Laurent Caraffa, Jean Philippe Tarel, Pierre Charbonnier. The Guided Bilateral Filter: When the Joint/Cross Bilateral Filter Becomes Robust. IEEE Transactions on Image Processing, 2015, 24 (4), pp 1199-1208.*

(Continued)

*Primary Examiner* — Sean T Motsinger (57) ABSTRACT

A method to denoise low dose CT images without introducing blurriness is shown using cross directional bilateral filtering. Techniques are provided that (1) enhance low-radiation dosage images, beyond just reducing noise, and (2) may be combined with other approaches, such as adaptive exposure techniques and iterative reconstruction, for radiation dose reduction.

16 Claims, 4 Drawing Sheets

(56) References Cited

U.S. PATENT DOCUMENTS

| | | |
|---|---|---|
| 2013/0051516 A1 | 2/2013 | Yang et al. |
| 2013/0089247 A1 | 4/2013 | Mercuriev |
| 2013/0202080 A1 | 8/2013 | Yu et al. |
| 2014/0270053 A1 | 9/2014 | Larson |
| 2015/0201895 A1 | 7/2015 | Suzuki |
| 2015/0317777 A1* | 11/2015 | Koehler .................. G06T 5/002 |
| | | 382/261 |
| 2017/0169564 A1 | 6/2017 | Hansen et al. |
| 2017/0178366 A1 | 6/2017 | Wang et al. |
| 2018/0033156 A1* | 2/2018 | Lee ........................... G06T 7/44 |

OTHER PUBLICATIONS

Notification of Transmittal of the International Search Report and the Written Opinion of the International Searching Authority, or the Declaration dated Jul. 9, 2019 in connection with International Patent No. PCT/US2019/026042, 8 pages.

Notification of Transmittal of the International Search Report and the Written Opinion of the International Searching Authority, or the Declaration dated Jun. 24, 2019 in connection with International Patent Application No. PCT/US2019/025777, 7 pages.

Armando Manduca, "Projection space denoising with bilateral filtering and CT noise modeling for dose reduction in CT", Medical Physics, vol. 36, No. 11, Nov. 2009, p. 4911-4919.

Tomasi et al. "Bilateral Filtering for Gray and Color Images", Proceedings of the 1998 IEEE International Conference on Computer Vision, Jan. 1998, 8 pages.

Eisemann et al. "Flash Photography Enhancement via Intrinsic Relighting", ACM Transactions on Graphics (TOG), vol. 23, No. 3, Aug. 2004, pp. 673-678.

Yu et al, "Radiation dose reduction in computed tomography: techniques and future perspective", Imaging Med., vol. 1, No. 1, Oct. 2009, pp. 65-84.

Non-final Office Action in connection with U.S. Appl. No. 16/375,508 dated Sep. 16, 2020, 18 pages.

* cited by examiner

CROSS DIRECTIONAL BILATERAL FILTER FOR CT RADIATION DOSE REDUCTION

PRIORITY CLAIM

This application claims priority to U.S. Provisional Patent Application No. 62/652,787 filed Apr. 4, 2018 and entitled PRE-FILTERED THREE-DIMENSIONAL BILATERAL FILTER and U.S. Provisional Patent Application No. 62/654,158 filed Apr. 6, 2018 and entitled CT IMAGE NOISE REDUCTION BY THE USE OF PRE-FILTERED THREE-DIMENSIONAL BILATERAL FILTER. The content of the above-identified patent document(s) is incorporated herein by reference, together with the contents of any references cited either in the above-identified patent document(s) or herein.

TECHNICAL FIELD

The present application relates generally to computed tomography scan image noise and, more specifically, to reducing noise in x-ray computed tomography medical images.

BACKGROUND

Computed tomography (CT) scanning is a diagnostic imaging technique providing detailed representations of internal organs, bones, and soft tissue of the human body, in which cross-sectional data derived from a CT scan is reformatted in multiple planes to generate three-dimensional (3D) representations for human viewing. CT scanning is often used, for example, to determine the presence, size, and location of a cancer tumor or diagnose internal injuries and/or bleeding.

For CT imaging, there is a tradeoff between radiation dosage levels and image quality. Generally, higher radiation doses result in higher signal-to-noise ratio and higher resolution images with fewer artifacts, while lower doses lead to increased image noise and more artifacts and less-sharp images. However, the higher radiation may increase the risk of adverse side effects, e.g., increasing the risk of radiation-induced cancer. As a result, low dose radiation CT is being studied with the hope of improving image quality without increasing the chances of potential adverse side effects.

Yet, despite recent developments in radiation dose reduction techniques in CT scanning—for example, techniques such as adaptive exposure and iterative reconstruction—current radiation dosing is still very high compared to traditional x-rays. A chest x-ray, for example, delivers 0.1 milli-Sievert (mSv), while a chest CT delivers 7 mSv—that is, 70 times as much. As such, there continues to be public concern about radiation risks from current CT radiation levels. In response, the techniques of the present disclosure provide a way of using low-dose CT imaging with vastly improved image quality of the type obtained with higher-dose CT scanning.

SUMMARY

Techniques for converting low-dose (LD) CT data to higher quality, lower noise images, such as for example, higher-dose (HD) like CT data, are provided. The techniques rely upon a cross bilateral filtering in a subspace of the data domain using a data smoothed in an orthogonal subspace. By applying the smoothing and cross bilateral filtering in orthogonal subspaces, the blurriness from the smoothed data does not propagate to the output CT images.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; and the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

FIGS. 1 through 5, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged data processing system connected to generate or receive, process, and display CT scan image data.

It is important to develop a technology to reduce CT radiation doses with preserving CT image quality. To make it happen by image processing techniques, it is necessary to denoise CT images with preserving edge information. Bilateral filter is a technique to smooth images while preserving edges. The general use of a bilateral filter with CT image data results in "spiked noise remaining" and the existence of "unnatural noise texture."

To resolve the problems of a bilateral filter, the cross bilateral filter can be used. A cross bilateral filter is a variant of the bilateral filter that decouples the notion of edges to be preserved from the remainder of the image to be smoothed. Many researchers have proposed using different images (such as flash images, simply smoothed images, etc.) as a second image E. For example, when simply smoothed images are used as a second image E, the blurriness of the image propagates to the output of the cross bilateral filter. The blurriness of CT images is normally not accepted by radiologists.

Figure 1:
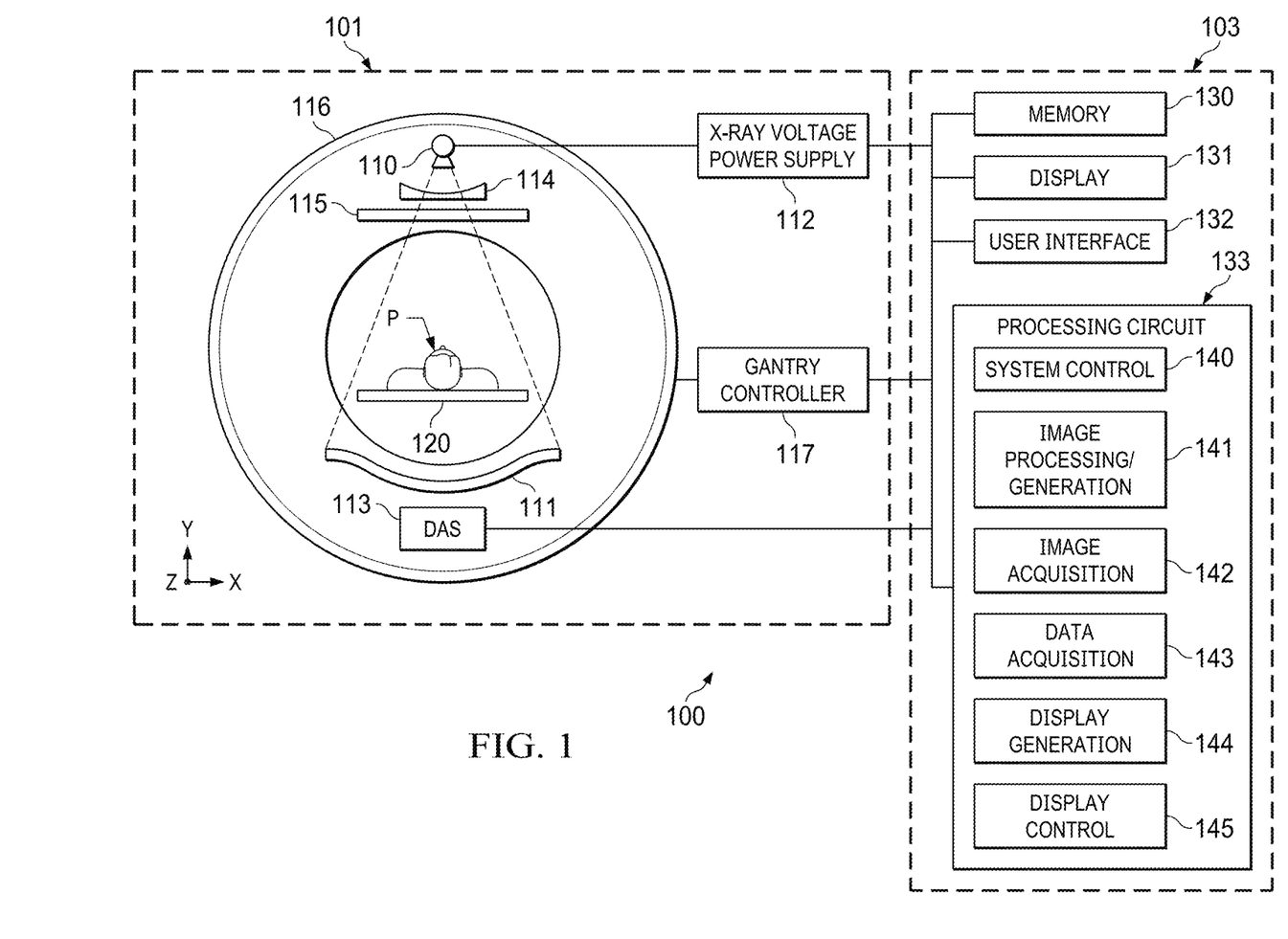
FIGS. 1 and 1A are diagrams of the overall configuration of a medical imaging and diagnosis system using cross directional bilateral filtering according to embodiments of the present disclosure.
Figure 1A:
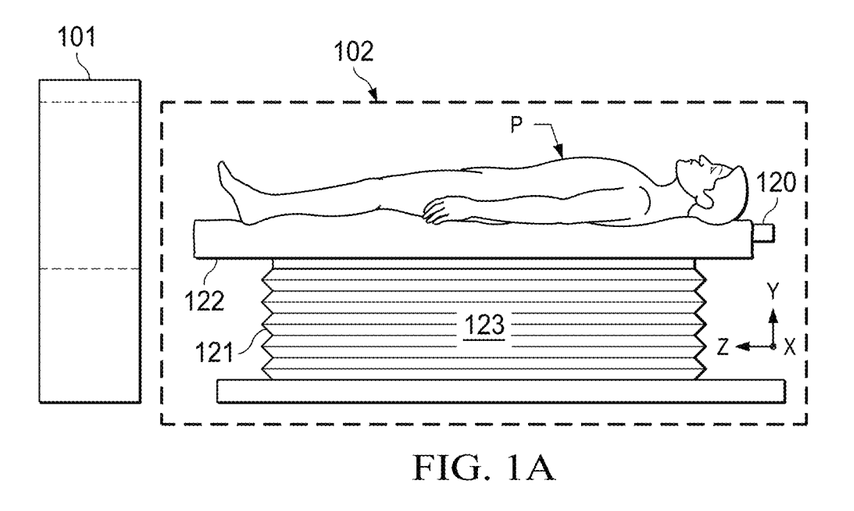

FIGS. 1 and 1A are diagrams of the overall configuration of a medical imaging and diagnosis system using cross directional bilateral filtering according to embodiments of the present disclosure. FIG. 1 is in the nature of a schematic and/or block diagram, while FIG. 1A illustrates portions of FIG. 1 somewhat more pictorially. In the following description, an x-ray CT system is described as an example of the medical imaging and diagnosis system 100. However, the techniques of the present disclosure could be adapted to other systems.

The medical imaging and diagnosis system (x-ray CT system) 100 includes a gantry 101, a bed assembly 102, and a console 103. The gantry 101 is a device configured to acquire information on internal portions of a subject P to be examined or treated, in order to generate a medical image of those internal portions of the subject P. The bed 102 is a device on which the subject P is placed. The console 103 is connected and configured to control the entire medical imaging and diagnosis system 100, including the gantry 101 and the bed 102.

The gantry 101 includes an x-ray generator 110, an x-ray detector 111, an x-ray high-voltage power supply 112, a data acquisition system (DAS) 113, a wedge 114, a collimator 115, a rotating frame 116, and a controller 117. The x-ray generator 110 includes an x-ray tube (vacuum tube) that, for example, in response to the supply of high voltage from the x-ray high-voltage power supply 112, irradiates thermoelectrons from a cathode (or "filament") to an anode (or "target"). The x-ray detector 111 detects x-rays irradiated from the x-ray generator 110 that have passed through (or around) the subject P. The x-ray detector 111 outputs an electrical signal to the DAS 113 corresponding to the amount of the x-rays detected. The x-ray detector 111 includes, for example, a plurality of x-ray detection element arrays each including a plurality of x-ray detection elements are arranged in the channel direction along one circular arc around the focus of the x-ray tube within the x-ray generator 110. The x-ray detector 111 has a structure in which, for example, the x-ray detection element arrays, where the x-ray detection elements are arranged in the channel direction, are arrayed in a slice direction to generate a medical image of a cross-sectional portion of the subject P. The x-ray detector 111 may be, for example, an indirect-conversion detector that includes a grid, a scintillator array, and an optical sensor array. The scintillator array has a plurality of scintillators each formed of scintillation crystals that emit light with a number of photons corresponding to the incident x-ray amount. The grid of the x-ray detector 111 is arranged on a surface of the scintillator array on the side where x-rays are incident, and includes an x-ray shielding plate having the function of absorbing scattered x-rays. The optical sensor array has the function of converting x-rays into electric signals corresponding to the amount of light from the scintillator array. The optical sensor array includes, for example, an optical sensor such as a photomultiplier tube (PMT).

Alternatively, the x-ray detector 111 may be a direct-conversion detector having a semiconductor element that converts incident x-rays into electric signals.

The x-ray high-voltage power supply 112 is provided with electric circuits such as a transformer and a rectifier, and includes a high-voltage generator having the function of generating a high voltage to be applied to the x-ray generator 110, as well as an x-ray controller that controls the output voltage according to x-rays irradiated by the x-ray generator 110. The high-voltage generator 112 may be of transformer type or inverter type. The x-ray high-voltage power supply 112 may be arranged on the rotating frame 116 or on the side of a fixed frame (not illustrated) of the gantry 101, which fixed frame rotatably supports the rotating frame 116.

The DAS 113 includes at least an amplifier and an analog-to-digital (A/D) converter. The amplifier amplifies an electric signal output from each of the x-ray detection elements of the x-ray detector 111, while the A/D converter converts the electric signal into a digital signal. The DAS 113 generates detection data (pure raw data) that is sent to the console 103.

The wedge 114 (also sometimes called a "wedge filter" or a "bow-tie filter") is a filter for adjusting the dose of x-rays irradiated from the x-ray generator 110. Specifically, the wedge 114 attenuates x-rays irradiated from the x-ray generator 110 as the x-rays pass therethrough, such that the subject P is irradiated with the x-rays of a predetermined distribution. The wedge 114 is made of, for example, aluminum processed so as to have a predetermined target angle or a predetermined thickness.

The collimator 115 includes lead plates or the like for narrowing the irradiation range of the x-rays having passed through the wedge 114, forming a slit by a combination of a plurality of lead plates or the like.

The rotating frame 116 supports the x-ray generator 110 and the x-ray detector 111 arranged therein at positions facing each other. The rotating frame 116 is an annular frame that rotates the x-ray generator 110 and the x-ray detector 111 according to a signal from the controller 117. In addition to the x-ray generator 110 and the x-ray detector 111, the rotating frame 116 may also support the x-ray high-voltage power supply 112 and the DAS 113 arranged therein. With this structure, the rotating frame 116 performs imaging while the x-ray generator 110 and the x-ray detector 111 are rotated together integrally around the subject P at the center of rotation, irradiating the subject P with x-rays from different angles and detecting the x-rays that have passed through the subject P. The rotating frame 116 is provided with an annular opening to let the subject P resting on top plate 120 to enter and exit.

The rotating frame 116 may be provided with a transmitter having a light emitting diode (LED) to transmit detection data generated by the DAS 113 to a receiver via optical communication. The receiver has a photodiode provided in a non-rotating part of the gantry 101 such as, for example, the fixed frame (not shown). The detection data received by the receiver is sent to the console 103. The detection data need not necessarily transmitted via optical communication from the rotating frame 116 to the non-rotating part of the gantry 101, and any method can be employed as long as non-contact data transmission is implemented.

As illustrated in FIG. 1, the rotation axis of the rotating frame 116 is generally aligned in a direction parallel to the longitudinal direction of the top plate 120 of the bed assembly 102, which is defined as the z-axis direction of a Cartesian coordinate system. An axial direction perpendicular to the z-axis direction and horizontal to the floor surface is defined as the x-axis direction, while an axial direction perpendicular to the z-axis direction and vertical to the floor surface is defined as the y-axis direction.

The gantry controller 117 includes a processing circuit having a central processing unit (CPU) and the like, and driving mechanisms such as motor(s) and actuator(s). The gantry controller 117 has the function of controlling the operation of the gantry 101 and the bed 102 in response to an input signal from a user input interface attached to the console 103 or the gantry 101. Upon receipt of an input signal, for example, the gantry controller 117 controls the rotating frame 116 to rotate, controls the gantry 101 to tilt, or controls the top plate 120 within the bed assembly 102 to move. The gantry controller 117 may be located in the gantry 101 or may be located in the console 103. The gantry controller 117 tilts the gantry 101 by rotating the rotating frame 116 about an axis parallel to the x-axis direction based on tilt angle information provided through the user input interface attached to the gantry 101.

The bed assembly 102 is a device on which the subject P to be scanned is placed, and moves the subject P. The bed assembly 102 includes a base 121, the top plate 120, a support frame 122, and a bed driving device 123. The base 121 supports the support frame 122 (which includes the top plate 120) movably in the vertical direction (they direction indicated by the arrow in FIG. 1) in the frame of the bed assembly 102. The top plate 120 is a plate on which the subject P is placed. The support frame 122 supports the top plate 120 on its upper surface. The bed driving device 123 is a motor and/or actuator to move the top plate 120 on which the subject P is placed in the longitudinal (z) direction of the top plate 120 or in the vertical (y) direction (vertical direction with respect to the floor surface). The bed driving device 123 is driven in response to an input signal from the console 103, and moves the top plate 120 in one or more of the directions described above. In addition to the top plate 120, the bed driving device 123 may also move the support frame 122 in the longitudinal direction of the top plate 120. Since the bed driving device 123 is located inside the base 121, it is illustrated by broken lines in FIG. 1.

The console 103 includes a memory 130, a display 131, a user input interface 132, and processing circuitry 133. The memory 130 is implemented by, for example, a semiconductor memory element such as a random access memory (RAM) or a flash memory, a hard disk, an optical disk, or the like. The memory 130 stores, for example, raw detection data, projection data and/or reconstructed image data. The display 131 displays various types of information such as, for example, medical images (CT images) generated by the processing circuit 133, a graphical user interface (GUI) for displaying system information to and receiving various instructions from the operator, and the like. The display 131 is formed of, for example, a touch-screen liquid crystal display (LCD) or the like. The user input interface 132 receives various types of input from the operator, converting those input(s) into electric signal(s) that are outputs to the processing circuitry 133 and or the motors and/or actuators mentioned above. For example, the user input interface 132 receives, from the operator, collection conditions for collecting projection data, reconstruction conditions for reconstructing a CT image, image processing conditions for generating a post-processing image from the CT image, and the like. The user input interface 132 is realized by, for example, a mouse, trackball, trackpad, and/or touchscreen; a keyboard; dedicated switches and/or buttons; a joystick; or some combination thereof.

The processing circuitry 133 controls the operation of the entire medical imaging and diagnosis system 100 according to the electrical signal(s) input at the user input interface 132 and various electrical feedback and control signals. The processing circuitry 133 implements, for example, system control 140, image processing/generation 141, image acquisition 142, data acquisition 143, display generating 144, and display control 145. System control 140 controls various functions of the processing circuitry 133 based on input(s) received from the operator through the user input interface 132. In some embodiments, image processing/generation 141 performs preprocessing, reconstruction, and image processing. The preprocessing operates on data output from the DAS 113 by processing such as logarithmic conversion, offset correction, inter-channel sensitivity correction, beam hardening correction, and the like. Note that data before preprocessing and data after preprocessing may sometimes be collectively referred to as "projection data." Reconstruction generates CT image data by reconstructing the projection data generated by the preprocessing function using a filtered back projection method, a successive approximation reconstruction method, or the like. Image processing converts the CT image data generated by the reconstruction function into three-dimensional image data or tomographic image data of an arbitrary cross section by a known method based on an input received from the operator through the user input interface 132. Image acquisition 142 acquires medical image data of a scan. More specifically, the image acquisition 142 acquires medical image data selected from medical image data (or "medical image") generated by the image processing/generation 141 based on a selection operation by the operator.

Based on medical image data acquired by image acquisition 142, data acquisition 143 acquires pixel value data contained in the medical image data. The pixel value data is acquired with respect to each region set by the operator. Display generation 144 generates display information based on the pixel value data. The display information is generated with respect to each region set by the operator as described above. Display control 145 causes displays on the display 131 of a CT image (medical image) based on CT image data acquired by image acquisition 142. The display conditions of the medical image are set according to an input signal provided by the operator through the user input interface 132. Display control 145 also displays the display information in a corresponding area of medical image data (representative image), and displays the display information in a predetermined display range, processing the display information in various display modes according to the conditions set by the operator.

In addition to the above-described functions, the processing circuitry 133 may have, for example, a scan control function that controls the driving of each part of the gantry 101 and/or the bed assembly 102 according to various conditions of scanning (imaging of the subject) provided through the user input interface 132.

In the above description of the overall configuration of the medical imaging and diagnosis system 100 of one embodiment, system control 140, image processing/generation 141, image acquisition 142, data acquisition 143, display generation 144 and display control 145 may optionally be implemented by computer executable programs, which are stored in a memory circuit such as, for example, the memory 130 and read from the memory circuit and executed by the processing circuitry 133 to realize the corresponding function described herein. In other words, having read the programs, the processing circuitry 133 implements the functions for the modules illustrated in FIG. 1. However, although the processing circuitry 133 may be implemented by a single programmable processor, it is not so limited. Instead, the processing circuitry 133 may be formed of a combination of a plurality of independent processors, each of which executes a program to realize corresponding one of the functions. Alternatively, dedicated hardware circuitry (or partially programmable circuitry) may be implemented, in one integrated circuit or in a plurality of integrated circuits, for each module depicts or for some combination of such modules. In addition, the programs each corresponding to one of the functions are described as being stored in a single memory circuit (the memory 130), but can instead be stored in a plurality of memory circuits arranged in a distributed manner, and the processing circuit may read each of the programs from each of the memory circuits.

In accordance with the present disclosure, a medical image acquired by the medical imaging and diagnosis system 100 has two main characteristics: the space domain S, which is the set of possible positions in a data and which is related to the resolution, i.e., the number of rows, columns, and depths in the typical CT data; and the range domain $\mathcal{R}$ which is the set of possible pixel values (where the number of bits used to represent the pixel value may vary). Common CT pixel representations are two bytes signed integers.

Figure 2:
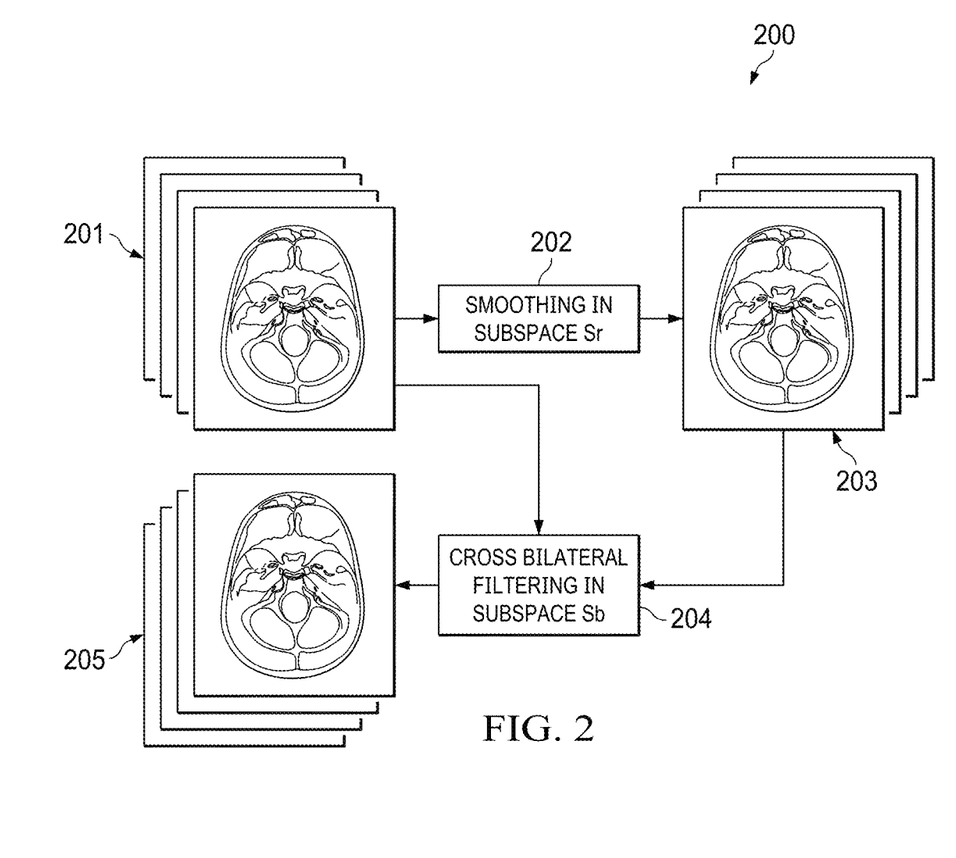
FIG. 2 illustrates 3D CT image noise reduction using cross directional bilateral filter(s) in accordance with embodiments of the present disclosure.

FIG. 2 illustrates 3D CT image noise reduction using cross directional bilateral filter(s) in accordance with embodiments of the present disclosure, performed within the processing circuitry 133 of the medical imaging and diagnosis system 100. In the present disclosure, a cross directional bilateral filter, which is a type of cross bilateral filtering, is employed to calculate bilateral filtering in $S_b$, which is a subspace of S, using a second data smoothed in another subspace $S_r$ that is orthogonal to $S_b$. By such filtering in orthogonal subspaces, it becomes possible to denoise data without influence of blurriness caused by smoothing in $S_r$.

Ordinal bilateral filtering is a technique to smooth images while preserving edges. The bilateral filter is defined as a weighted average of pixel, which takes into account the variation of intensities to preserve edges, and it is defined by:

$$BF[I]_p = \frac{1}{W_p} \sum_{q \in S} G_{\sigma_s}(\|p-q\|) G_{\sigma_r}(I_p - I_q) I_q \qquad (1)$$

where $W_p$ is a normalization factor:

$$W_p = \Sigma_{q \in S} G_{\sigma_s}(\|p-q\|) G_{\sigma_r}(I_p - I_q). \qquad (2)$$

Here, I indicates a S dimensional input data, p and q are S dimensional vectors, $I_p$ indicates the value of I at the location of p, $I_Q$ indicates the value of I at the location of q, and $G_{\sigma_s}$ and $G_{\sigma_r}$ are Gaussian functions being applied to space and range filtering, respectively.

Cross bilateral filtering is a variant of bilateral filtering that decouples the notion of edges to preserve from the image to smooth. Given an image I, the cross bilateral filter smooths I while preserving the edges of a second image E. In practice, the range weight is computed using E instead of I:

$$CBF[I, E]_p = \frac{1}{W_p} \sum_{q \in S} G_{\sigma_s}(\|p-q\|) G_{\sigma_r}(E_p - E_q) I_q, \qquad (3)$$

where $$W_p = \sum_{q \in S} G_{\sigma_s}(\|p-q\|) G_{\sigma_r}(E_p - E_q). \qquad (4)$$

It has been proposed to use different images as a second image E, such as flash images, simply smoothed images, etc.

In the present disclosure, cross directional bilateral filtering, which calculates bilateral filtering in $S_b$, a subspace of S, uses second data smoothed in another subspace $S_r$ orthogonal to $S_b$. By the present disclosure, it becomes possible to denoise data without influence of blurriness by smoothing in $S_r$.

The cross directional filter can be described as follows;

$$CDBF[I, E]_p = \frac{1}{W_p} \sum_{q \in S} G_{\sigma_s}(\|p-q\|_{S_b}) G_{\sigma_r}(E_p - E_q) I_q, \qquad (5)$$

where $$W_p = \sum_{q \in S} G_{\sigma_s}(\|p-q\|_{S_b}) G_{\sigma_r}(E_p - E_q), \qquad (6)$$

$$E_p = \sum_{q \in S} G_{\sigma_t}(\|p-q\|_{S_r}) I_q. \qquad (7)$$

and subspaces $S_b$ and $S_r$ are orthogonal to each other, $\|p-q\|_{S_b}$ indicates the distance of p and q in subspace $S_b$, and $\|p-q\|_{S_r}$ is the distance of p and q in subspace $S_r$.

For example, with three-dimensional data such as original CT volume data I 201, $S_b$ can be x-y two-dimensional subspace and $S_r$ can be z, which is a one-dimensional subspace. First, a z directional smoothing 202 is applied to the original CT volume data I using equation (7), to produce smoothed data E 203. Then, using the z directionally smoothed data 203 as a smoothed second data E, cross directional bilateral filtering 204 is applied in x-y subspace using equation (5), or:

$$CDBF[I, E]_p = \frac{\sum_{q \in S} G_{\sigma_s}(\|p-q\|_{S_b}) G_{\sigma_r}(E_p - E_q) I_q}{\sum_{q \in S} G_{\sigma_s}(\|p-q\|_{S_b}) G_{\sigma_r}(E_p - E_q)}, \qquad (8)$$

when equation (6) is substituted into equation (5). Note that the terms $E_p - E_q$ in equation (8) are employed to calculate contrast. By doing this, the z directional blur of pre-filtering is hard to propagate to the x-y plane and the signals including edge information in x-y plane are kept well in the smoothed, filtered output 205.

Figure 3:
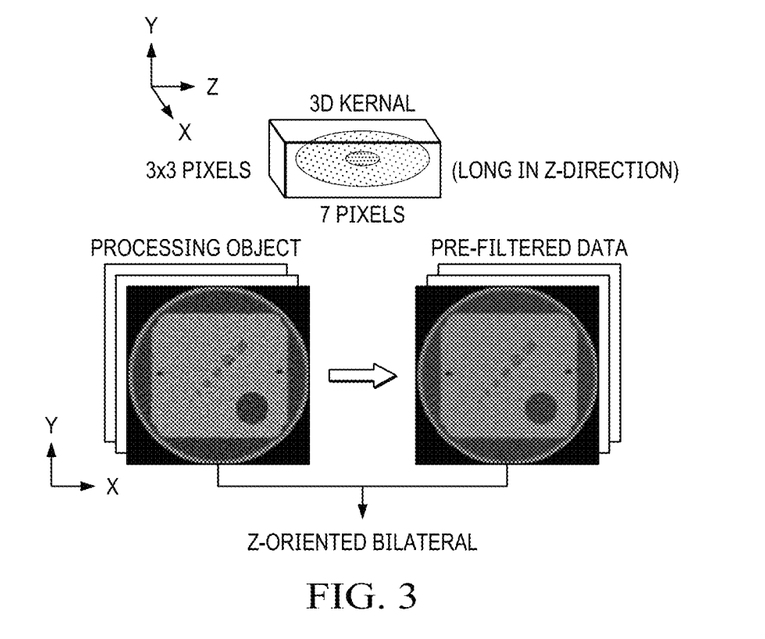
FIG. 3 illustrates one example of using cross directional bilateral filtering in accordance with FIG. 2.

FIG. 3 illustrates one example of using cross directional bilateral filtering in accordance with FIG. 2. In this example, the smoothing is applied in x-y space and then the bilateral filtering is applied to the z direction as described above. Thus, for example, the 3D kernel within the processing circuitry 133 may process the projection data and/or the medical image data using data blocks that are 3×3 pixels in the x-y plane and 7 pixels in the z direction. Blur of the x-y filtering is difficult to propagate to the z direction.

Figure 4:
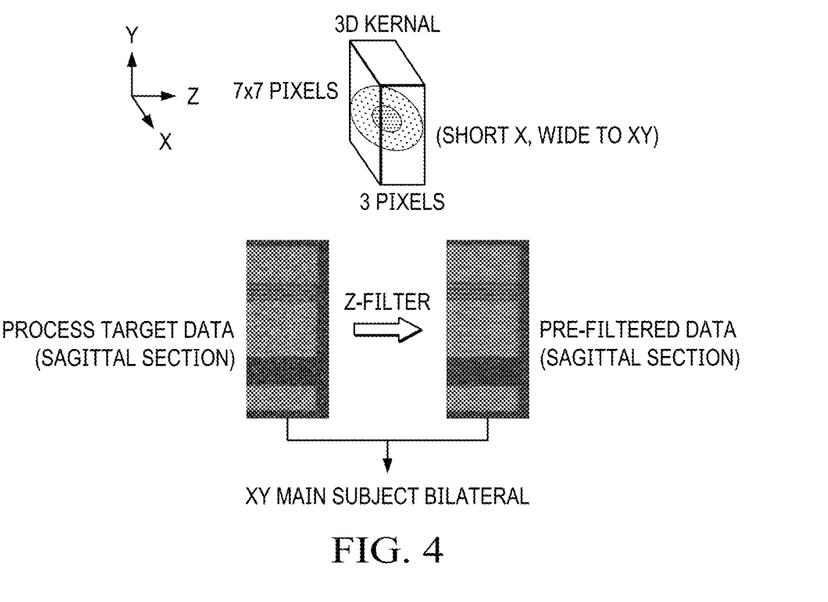
FIG. 4 illustrates another example of using cross directional bilateral filtering in accordance with FIG. 2.

FIG. 4 illustrates a second example of using cross directional bilateral filtering in accordance with FIG. 2. In this example, the smoothing is applied in z direction and then the bilateral filtering is applied in the x-y space. That is, in one alternative, $S_b$ can be the z one-dimensional subspace and $S_r$ can be the x-y plane, which is a two-dimensional subspace. In this embodiment, the 3D kernel within the processing circuitry 133 may process the projection data and/or the medical image data using data blocks that are short (3 pixels) in the z direction and wide (7×7 pixels) in the x-y plane.

First, a z directional smoothing is applied to the data. Then, using the z directionally smoothed data as a second data, cross bilateral filtering is applied in x-y subspace. By this, the z directional blur of smoothing is hard to propagate to the x-y space and the signals including edge information in z direction are kept well in the output.

Another example is as follows: $S_b$ can be an x one-dimensional subspace and $S_r$ can be y, which is another one-dimensional subspace. First, a y directional smoothing is applied to the data. Then, using the y directionally smoothed data as a pre-filtered second data, cross bilateral filtering is applied in the x direction. By doing this, the y directional blur of pre-filtering is hard to propagate to the x direction and the signals including edge information in z direction are kept well in the output.

Equation (7) is a Gaussian kernel, but a rectangle function could also be used instead of a Gaussian kernel. Also, instead of linear smoothing filters, nonlinear smoothing filters such as median filters may be employed.

Figure 5:
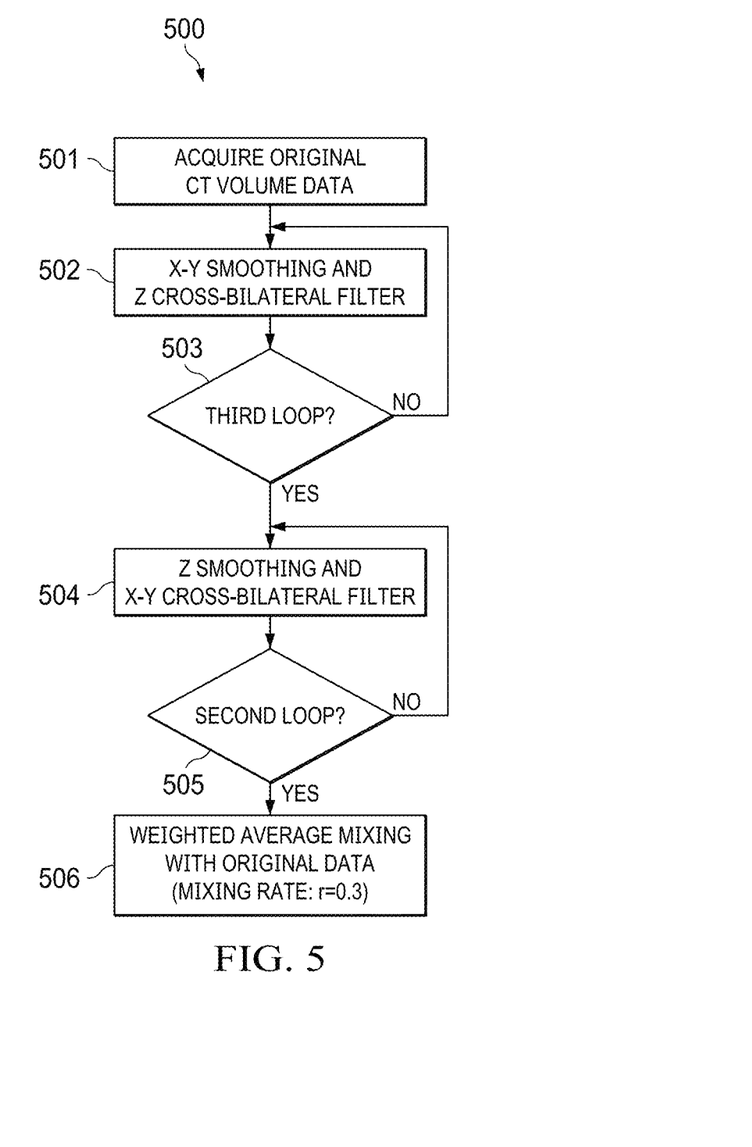
FIG. 5 is a high level flowchart for an exemplary process of combinational usage of cross directional bilateral filters in accordance with an embodiment of the present disclosure.

FIG. 5 is a high level flowchart for an exemplary process of combinational usage of cross directional bilateral filters in accordance with an embodiment of the present disclosure. The process 500 is executed within the processing circuitry 133 of the medical imaging and diagnosis system 100. The process 500 is useful for denoising low dose CT images without introducing blurriness, thereby enhancing the low dose CT data to provide image quality comparable to higher does CT data. The process 500 begins with acquiring original CT volume data (step 501). First, x-y smoothing and z cross bilateral filtering is performed (step 502) three times (step 503) on the original CT volume data or on the output of a prior iteration of the x-y prefiltering and z cross bilateral filtering. Then, z smoothing and x-y cross bilateral filtering is performed (step 504) twice (step 504), first on the output of the three iterations of x-y smoothing and z cross bilateral filtering and then on the output of the first iteration of z smoothing and x-y cross bilateral filtering. The output of those two iterations of z smoothing and x-y cross bilateral filtering is filtered CT volume data. The filtered CT volume data is then mixed with weighting average (using a mixing ratio r=0.3) with the original CT volume data (step 506). The output of that mixing is processed CT volume data. The resulting processed CT volume data may then be further processed as appropriate to generate medical images for display on

REFERENCES

TOMASI, C., AND MANDUCHI, R. 1998. Bilateral filtering for gray and color images. In Proc. IEEE Int. Conf. on Comp. Vision.

EISEMANN, E., AND DURAND, F. 2004. Flash photography enhancement via intrinsic relighting. ACM Trans. on Graphics 23, 3. Proc. of ACM SIGGRAPH conf.

Yu, L., Liu, X., et al. Radiation dose reduction in computed tomography: techniques and future perspective, Imaging Med. Pp. 65-84 (2009).

Although the present disclosure has been described with exemplary embodiments, various changes and modifications may be suggested to one skilled in the art. It is intended that the present disclosure encompass such changes and modifications as fall within the scope of the appended claims.

What is claimed is:

1. An image processing method, the method comprising:
smoothing N-dimensional input computed tomography (CT) image data I in a subspace $S_r$ to create a second image E; and
cross bilateral filtering the N-dimensional input CT image data I in a subspace $S_b$ that is orthogonal to the subspace $S_r$ using the second image E.

2. The image processing method of claim 1, wherein the N-dimensional input CT image data is one of two-dimensional CT image data, three-dimensional CT image data, or four-dimensional temporal sequence CT image data.

3. The image processing method of claim 1, wherein the N-dimensional input CT image data is one of x-ray, magnetic resonance imaging (MRI), or other medical image data.

4. The image processing method of claim 1, wherein the smoothing employs one of a simple linear smoothing filter, a nonlinear filter, or a bilateral filter.

5. The image processing method of claim 4, wherein the simple linear smoothing filter is a Gaussian filter.

6. The image processing method of claim 4, wherein the nonlinear filter is a median filter.

7. The image processing method of claim 1, wherein the smoothing and the cross bilateral filtering are repeated multiple times to generate a medical image.

8. The image processing method of claim 1, wherein the smoothing of the N-dimensional input CT image data I in the subspace $S_r$ and the cross bilateral filtering of the N-dimensional input CT image data I in a subspace $S_b$ using the second image E produces interim N-dimensional processed CT image data, the method further comprising:
smoothing the interim N-dimensional processed CT image data in the subspace $S_b$ to create a third image E'; and
cross bilateral filtering the interim N-dimensional processed CT image data in the subspace $S_r$ using the third image E'.

9. An image processing system, comprising:
processing circuitry configured to
smooth N-dimensional input computed tomography (CT) image data I in a subspace $S_r$ to create a second image E, and
cross bilateral filtering the N-dimensional input CT image data I in a subspace $S_b$ that is orthogonal to the subspace $S_r$ using the second image E; and
a display configured to display a medical image based on the cross bilateral filtered N-dimensional input CT image data I.

10. The image processing system of claim 9, wherein the N-dimensional input CT image data is one of two-dimensional CT image data, three-dimensional CT image data, or four-dimensional temporal sequence CT image data.

11. The image processing system of claim 9, wherein the N-dimensional input CT image data is one of x-ray, magnetic resonance imaging (MRI), or other medical image data.

12. The image processing system of claim 9, wherein the smoothing employs one of a simple linear smoothing filter, a nonlinear filter, or a bilateral filter.

13. The image processing system of claim 12, wherein the simple linear smoothing filter is a Gaussian filter.

14. The image processing system of claim 12, wherein the nonlinear filter is a median filter.

15. The image processing system of claim 9, wherein the smoothing and the cross bilateral filtering are repeated multiple times to generate the medical image.

16. The image processing system of claim 9, wherein the smoothing of the N-dimensional input CT image data I in the subspace $S_r$ and the cross bilateral filtering of the N-dimensional input CT image data I in a subspace $S_b$ using the second image E produces interim N-dimensional processed CT image data, the processing circuitry further configured to:
smooth the interim N-dimensional processed CT image data in the subspace $S_b$ to create a third image E', and
cross bilateral filter the interim N-dimensional processed CT image data in the subspace $S_r$ using the third image E'.

* * * * *